United States Patent [19]

Gozzo et al.

[11] 4,311,516

[45] Jan. 19, 1982

[54] METHOD OF COMBATTING PLANTS WHICH INFEST MAIZE CULTIVATIONS WITHOUT DAMAGING THE MAIZE

[75] Inventors: Franco Gozzo; Luigi Abbruzzese; Giorgio Siddi, all of Milan, Italy

[73] Assignee: Montedison S.p.A., Milan, Italy

[21] Appl. No.: 139,091

[22] Filed: Apr. 10, 1980

Related U.S. Application Data

[60] Continuation-in-part of Ser. No. 98,788, Nov. 30, 1979, abandoned, and a continuation-in-part of Ser. No. 971,713, Dec. 21, 1978, Pat. No. 4,228,101, which is a division of Ser. No. 846,351, Oct. 28, 1977, Pat. No. 4,195,036.

[30] Foreign Application Priority Data

Oct. 29, 1976 [IT] Italy .............................. 28867 A/76
Dec. 23, 1977 [IT] Italy .............................. 31189 A/77

[51] Int. Cl.³ ..................... A01N 37/44; A01N 37/18
[52] U.S. Cl. ........................................ 71/111; 71/118
[58] Field of Search ............................... 71/111, 118

[56] References Cited

U.S. PATENT DOCUMENTS 3,780,090  12/1973  Akiba et al. .......................... 71/115
3,867,444   2/1975  Baker .................................... 71/118
4,021,224   5/1977  Pallos et al. .......................... 71/118

*Primary Examiner*—Glennon H. Hollrah

[57] ABSTRACT

Plants which infest maize cultivations are successfully combatted without damage to the maize by treating the infested maize with herbicidal esters of N,N-disubstituted glycines and an antidote having the general formula

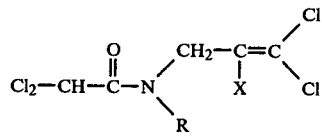

in which X is H or halogen; and R is H, $C_1$-$C_5$ alkyl, poly (haloalkyl), alkenyl, poly (haloalkenyl), alkinyl, (poly) haloalkinyl all containing carbon atoms in a number ranging from 2 to 5, or phenyl.

10 Claims, No Drawings

METHOD OF COMBATTING PLANTS WHICH INFEST MAIZE CULTIVATIONS WITHOUT DAMAGING THE MAIZE

This is a continuation-in-part of our application Ser. No 971,713 filed Dec. 21, 1978 (now U.S. Pat. No. 4,228,101); and of our pending application Ser. No. 98,788 filed Nov. 30, 1979 now abandoned as a Rule 60 Division of our application Ser. No. 846,351 filed Oct. 28, 1977 (now U.S. Pat. No. 4,195,036).

BACKGROUND OF THE INVENTION

Esters of glycine, substituted at the nitrogen atom, and having herbicidal properties are described in, for instance, U.S. Pat. No. 3,780,090 and German Patent Application No. 2,311,897.

More particularly, esters of N-(chloroacetyl)-N-(2,6-dialkylphenyl) glycine of the general formula:

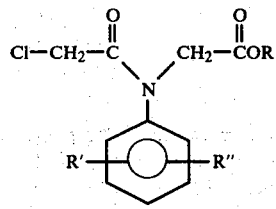

(I)

have been found to exert good herbicidal action on maize. However, those herbicides are rather noxious to maize and, therefore, it is not possible to use them in practice in maize cultivation.

French Patent Application No. 2,133,793 describes herbicidal compositions consisting of a herbicide (thiolcarbamates and substituted triazines being exemplified) and an antidote of the general formula:

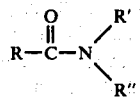

in which R may be, among others, a dichloromethyl group, and R' and R" represent numerous alkylene, alkyl, aryl groups, etc.). Such compositions permit the use of the thiolcarbamates and substituted triazines in the disherbing of maize and wheat fields without prejudice to the useful plants.

The following compounds proved to be very effective as disherbing agents:

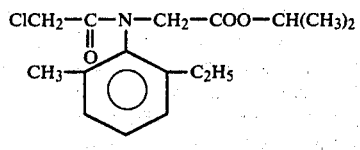

(HS 26910)

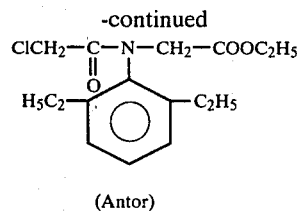

(Antor)

However they proved to be toxic even for plants of agricultural interest such as maize.

In German Patent Application DOS No. 2,402,983 there are described antidotes for agricultural cultivations against the toxic effect of chloroacetanylide type herbicides, of formula:

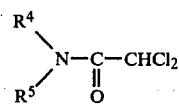

wherein $R^4$ and $R^5$ are, among others, alkyl, alkenyl, alkinyl optionally substituted by halogen atoms.

The compounds of formula:

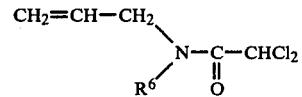

wherein $R^6$=allyl or alkyl, are cited as particularly effective antidotes.

In U.S. Pat. No. 4,033,756 there is described the use of dichloroacetamides in coating the seeds of crops such as rice and corn in order to protect them from injury by a variety of herbicides, particularly the thiocarbamates.

U.S. Pat. No. 4,021,224 describes herbicide compositions consisting of an herbicide (thiocarbamates or triazines) and an antidote of general formula:

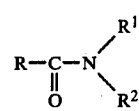

wherein R may be, among others, a dichloromethyl group while $R^1$ and $R^2$ represent alkyl, alkenyl and aryl groups.

German Patent Application DOS No. 2,747,814 describes antidotes of general formula:

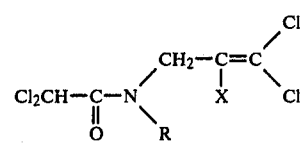

wherein
X=H, halogen
R=H, phenyl, optionally halogen-substituted alkyl, alkenyl or alkinyl groups.

Said products allow the use of non-selective herbicides, such as derivatives of N,N-disubstituted glycine in disherbing of maize and wheat fields without damaging the useful plants. Particularly active in protecting maize cultivations against the damages of HS 26910 and Antor, proved to be the compound N-allyl-N-(3,3-dichloroallyl)-dichloroacetamide of formula:

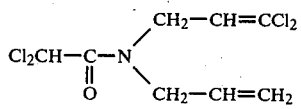

THE PRESENT INVENTION

An object of this invention is to provide a method for combatting infesting plants of a maize cultivation without damaging the maize by treating the infested maize with antidotes which exert a detoxicating action on maize, neutralizing the damages caused to maize cultivations by the herbicides of general formula (I).

Another object of this invention is that of providing a method for freeing maize cultivations from infesting weeds and herbs without harming the crop itself, and which consists in treating the cultivations with a non-selective herbicide in the presence of amounts of compounds of formula II ranging from 0.05 kg/ha upward.

This and other objects are accomplished by the present invention according to which the infested maize is treated with antidotes which are dichloroacetamides of the general formula:

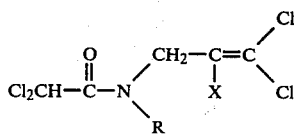

in which

X is H or halogen; and

R is H, alkyl having from 1 to 5 carbon atoms, (poly)-haloalkyl, alkenyl, (poly)-haloalkenyl, alkinyl, and (poly)-haloalkinyl containing a number of carbon atoms in the range from 2 to 5, or phenyl.

Unexpectedly, the detoxicating action on maize of the dichloroacetamides of formula (II) is up to ten times greater than that exerted by N-dialkyl-dichloroacetamide, the most active antidote described in French Patent Application No. 2,133,793.

The antidotes used in the practice of this invention which are N-(3,3-dichloro-2-X-alkyl) dichloroacetamides are partly, and generically, comprised in French Patent Application No. 2,133,793, when, in the general formula

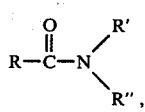

R is haloalkyl, R' is haloalkenyl and R" is haloalkenyl, alkyl, alkenyl, or phenyl. However, said dichloroacetamides are not described as chemical compounds in the French Patent Application No. 2,133,793. Moreover, no antidote activity with respect to herbicides of general formula (I) for the protection of maize is established in French Patent Application, nor is there any suggestion in the latter of the fact that the dichloroacetamides having formula (II) of this invention could have an antidote action decidedly superior to that developed by the compounds described therein.

The dichloroacetamides of formula (II) can be prepared by reacting a N-substituted-N-(3,3-dichloro-2-X-alkyl) amine with dichloroacetyl chloride in the presence of a HCl acceptor which may be an excess of the amine, at room temperature and optionally in an inert solvent, the reaction proceeding as follows:

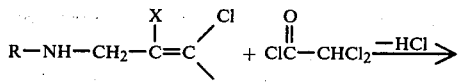

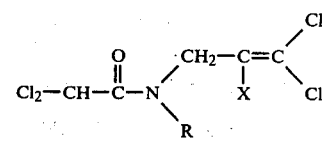

The starting amine is prepared by alkylation of the R—NH$_2$ amine with 1,3-trichloro-2-X-propene according to the equation:

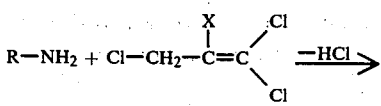

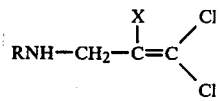

Said reaction is carried out in the presence of a HCl acceptor which may be an excess of the amine and, optionally, in an inert solvent.

The antidotes of the invention are compatible in all proportions (ratios) with the herbicidal compounds of general formula (I). They may be formulated in the presence of diatomite under the usual conditions suitable for obtaining powders, possibly in the presence of surfactants, both alone or in admixture with the compounds of general formula (I).

By methods known to the skilled in the art, the compositions may be formulated as suspensions or sprayable aqueous dispersions, in the presence of surfactants and/or solvents.

The activity of the antidote is perceptible in doses of 0.05 kg/ha in the presence of toxic doses (4 kg/ha) of the herbicides of general formula (I).

The following examples are given to illustrate the invention in more detail and are not intended to be limiting.

EXAMPLE 1

To 1.2 moles of allylamine dissolved in 200 ml of benzene, were added dropwise and under stirring at the boiling temperature of the mixture, 0.3 moles of 1,3,3-trichloropropene, diluted with 50 ml of the same solvent.

Once the addition was accomplished, the mixture was maintained at boiling for another 2 hours, after which it was washed with water and then dried.

After removal of the solvent, there remained an oil, N-allyl-N-(3,3-dichloroally)amine, which distills under reduced pressure: b.p. $_{18\ mm}$=79°–81° C.

To 0.04 mole of the amine thus obtained, dissolved in 50 ml of dichloroethane, there was added dropwise, under stirring, 0.02 mole of dichloroacetyl chloride, diluted with 20 ml of the same solvent.

After the addition had been accomplished, the mixture was maintained under stirring for a further 2 hours at room temperature. After removal of the solid that had formed (amine hydrochloride), the dried solution was subjected to evaporation. The residue, N-allyl-(3,3-dichloroallyl) dichloroacetamide, (our Mark M7601) which was a yellowish oil, was distilled under reduced pressure: $E_{0.4 \, mm} = 105°-8°$ C.

| Theor. % | Found % |
|---|---|
| Cl = 51.20 | 50.54 |
| C = 34.69 | 34.31 |
| H = 3.27 | 3.19 |
| N = 5.06 | 5.15 |

EXAMPLE 2

To 2 moles of methylamine (a 33% aqueous solution) was added, dropwise, at room temperature, 0.2 mole of 1,3,3-trichloropropene, dissolved in 120 ml of methanol. When the addition was terminated, the mixture was kept under stirring for another 3 hours and then was allowed to rest overnight.

By extraction of the reaction product with dichloromethane or with ethyl ether, followed by evaporation of the dried substances, there was obtained a yellowish oil, N-methyl-N-(3,3-dichloroallylamine), which distilled under pressure: $E_{15 \, mm} = 51°-52°$ C.

By reaction of this amine with dichloroacetyl chloride as in Example 1, N-methyl-N-(3,3-dichloroallyl)-dichloroacetamide (our ref. Mark M 7637), a yellow oil is obtained.

| Theor. % | Found % |
|---|---|
| Cl = 56.51 | Cl = 55.77 |
| C = 28.72 | C = 28.02 |
| H = 2.81 | H = 2.73 |
| N = 5.58 | N = 5.44. |

EXAMPLE 3

To 0.2 mole of hexamethylentetraamine dissolved in 300 ml of ethanol at 50° C. and under stirring, there was added 0.2 mole of NaI, then, dropwise, 0.2 mole of 1,3,3-trichloropropene.

After completion of the addition, the mixture was kept under stirring for another 2 hours and then allowed to stand for 24 hours.

After saturation with gaseous HCl, the mixture was allowed to stand for another 12 hours. After removal of the solid present, by filtration under vacuum, the liquid was evaporated. The residue, the amine hydrochloride, was washed with dichloromethane and then dried. It melted at between 215° and 217° C. The free amine, N-(3,3-dichloroallyl)amine, obtained from the hydrochloride by alkalinization of the aqueous solution and by extraction with ethyl ether, boiled at 53° C. under a pressure of 15 mm. Hg.

By reaction of the N-(3,3-dichloroallyl)amine with the dichloroacetyl chloride, as in Example 1, there was obtained N-(3,3-dichloroallyl)dichloroacetamide.

| Theor. % | Found % |
|---|---|
| Cl = 59.86 | Cl = 58.01 |
| C = 25.35 | C = 25.75 |
| H = 2.13 | H = 2.15 |
| N = 5.91 | N = 6.11. |

EXAMPLES 4 TO 7

Using the same process as in Example 2, there was obtained, from methylamine and 1,2,3,3-tetrachloropropene, N-methyl-N-(2,3,3-trichloroallyl)-amine, with b.p. $_{15 \, mm} = 67°$ C., and which, by reaction with dichloroacetyl chloride, yielded N-methyl-N-(2,3,3-trichloroallyl)-dichloroacetamide (Applicants' Mark M 8069), a yellow oil.

| Theor. % | Found % |
|---|---|
| Cl = 62.12 | Cl = 60.20 |
| C = 25.25 | C = 25.06 |
| H = 2.12 | H = 2.11 |
| N = 4.91 | N = 5.04. |

From ethylamine and 1,2,3,3-tetrachloropropene, proceeding as in Example 1, there was obtained N-ethyl-N-(2,3,3-trichloroallyl)-amine with b.p.$_{35 \, mm} = 91°$ C.-92° C.

From said product, by reaction with dichloroacetyl chloride, there was obtained N-ethyl-N-(2,3,3-trichloroallyl)-dichloroacetamide, (Applicants' Mark M 8280), as a yellow oil. The elementary percentual analysis gave:

| Theor. % | Found % |
|---|---|
| Cl = 59.21 | Cl = 58.74 |
| C = 28.08 | C = 28.09 |
| H = 2.69 | H = 2.72 |
| N = 4.67 | N = 4.40. |

By proceeding as in Example 1, from isopropylamine and 1,2,3,3-tetrachloropropene there was prepared N-isopropyl-N-(2,3,3-trichloroallyl)-amine: b.p.$_{18 \, mm} = 84°-85°$ C.

By reaction thereof with dichloroacetyl-chloride there was obtained N-isopropyl-N-(2,3,3-trichloroallyl)-dichloroacetamide (Applicants' Mark M 8281) having a melting point = 51°-52° C. (crystallized by n-hexane).

| Theor. % | Found % |
|---|---|
| Cl = 56.56 | Cl = 55.38 |
| C = 30.66 | C = 30.77 |
| H = 3.21 | H = 3.17 |
| N = 4.47 | N = 4.00. |

From propargylamine and 1,3,3-trichloropropene, proceeding as in Example 1, there was prepared N-propargyl-N-(3,3-dichloroallyl)amine: b.p.$_{15 \, mm} = 88°-91°$ C., from which, by reaction with dichloroacetyl chloride, there was obtained N-propargyl-N-(3,3-dichloroallyl)dichloroacetamide, (Applicants' Mark 8341), a yellowish oil.

| Theor. % | Found % |
|---|---|
| Cl = 51.57 | Cl = 50.52 |
| C = 34.94 | C = 34.81 |
| H = 2.56 | H = 2.67 |
| N = 5.09 | N = 4.81. |

EXAMPLE 8

Preparation of
N-(1,1-dimethylpropargyl)-N-(dichloroallyl)-dichloroacetamide (our mark: M 8991)

Into 1.2 moles of 1,1-dimethylpropargylamine there were dripped, under stirring at room temperature, 0.3 moles of 1,3,3-trichloropropene. Thereupon the ensuing mixture was maintained for 4 hours at boiling temperature. After cooling down, 100 ml of diethyl-ether were added to the mixture, then the mixture was washed with water and dried on anhydrous $Na_2SO_4$.

After removal of the solvent and the excess of amine, under vacuum in a rotatory evaporator, there remained an oil, N-(1,1-dimethylpropargyl)-N-(3,3-dichloroallyl)amine, which later on becomes a low-melting solid. Elemental analysis gave the following results:

| Theor. % | Found % |
|---|---|
| Cl = 36.92 | Cl = 35.98 |
| C = 50.02 | C = 48.42 |
| H = 5.77 | H = 6.15 |
| N = 7.29 | N = 7.18. |

To 0.04 moles of the amine thus obtained, dissolved in 150 ml of dichloroethane, wherein there had been suspended 0.05 moles of $NaHCO_3$, there were added dropwise and under stirring, at boiling temperature of the mixture, 0.04 moles of dichloroacetylchloride, diluted in 20 ml of the same solvent. Once the addition was completed, the mixture was maintained at the boiling temperature until development of $CO_2$ had ceased. After cooling down, the mixture was first washed with HCl (3% aqueous solution) and then with water.

By removal of the solvent from the solution previously dried on anhydrous $Na_2SO_4$, there was obtained N-(1,1-dimethylpropargyl)-N-(3,3-dichloroallyl)-dichloroacetamide, a low melting solid.

The elementary analysis showed the following composition:

| Theor. % | Found % |
|---|---|
| Cl = 46.79 | Cl = 43.59 |
| C = 39.64 | C = 40.79 |
| H = 3.66 | H = 3.86 |
| N = 4.62 | N = 4.47. |

The IR spectrum proved consistent with the assigned formula.

EXAMPLE 9

Preparation of
N-ethyl-N-(3,3-dichloroallyl)-dichloroacetamide (our mark: M 8990).

To 1.2 moles of ethylamine, dissolved in an equal volume of benzene, there were added dropwise and under stirring, at room temperature, 0.3 moles of 1,3,3-trichloropropene. Once the addition was completed, the mixture was maintained at the boiling point for 3 hours. After cooling down, the mixture was washed with water and thereupon dried on $Na_2SO_4$.

By removal of the solvent and the excess of ethylendiamine, there remained a liquid, N-ethyl-N-(3,3-dichloroallyl)-amine, which under a pressure of 15 mm distilled at between 61° C. and 63° C.

From this distillate, by the reaction of it with dichloroacetyl chloride, according to the procedures described in the preceding Example 8, there was obtained N-ethyl-N-(3,3-dichloroallyl)-dichloroacetamide, a brown oil.

The elementary analysis showed the following composition:

| Theor. % | Found % |
|---|---|
| Cl = 53.52 | Cl = 50.87 |
| C = 31.73 | C = 33.20 |
| H = 3.42 | H = 3.89 |
| N = 5.29 | N = 5.18. |

The IR spectrum proved consistent with the assigned formula.

EXAMPLE 10

To a series of pots with an upper diameter of 10 cm and a height of 10 cm, filled with sandy soil and in each of which there had been sown a certain infesting grass (see Table infra.) and maize, there was added water in the amount necessary for a good germination or sprouting of the seeds. Immediately thereafter a series of said pots was treated with the herbicide N-(2-methyl-6-ethyl-phenyl)-N-(isopropyl-carboxylmethyl)-chloroacetamide, (Applicants' Mark HS 26910); see formula I in which R is isopropyl, R' is methyl, and R" is ethyl) in the form of a hydroacetonic dispersion (20% vol/vol) in doses of 4 kg/ha of active principle by application on the surface of the soil, followed by covering with an additional layer of 0.5 cm of soil.

A second series of pots was treated, with the same dose and under the same conditions, with the herbicide N-(2,6-diethylphenyl)-N-(ethylcarboxymethyl)-chloroacetamide ("Antor", Hercules); see formula I in which R is ethyl and R' and R" are ethyl.

A third and fourth series of pots were treated, under the same conditions, with a hydroacetonic dispersion containing, respectively, the herbicide HS 26910 and herbicide "Antor", to each of which was added antidotes M7601 and, separately, M8069, in different proportions so as to obtain, in each instance, a dose of 4 kg/ha of herbicide together with a dose of from 0.1 to 0.8 kg/ha of one or the other of the antidotes of the invention.

For comparative purposes, a further two series of pots were treated under the same conditions with two hydroacetonic dispersions containing, respectively, herbicide HS 26910 and herbicide "Antor", each of which had been additioned with antidote N-diallyl-dichloroacetamide (Mark R 25788; Stauffer) in the same proportions as those applied with the two antidotes M7601 and M8069.

A seventh series of pots, in which only maize had been sown, was treated with a hydroacetonic dispersion of antidotes M7601 and M8069 only in doses varying from 0.1 to 0.8 Kg/ha. This application has no negative effect on the maize plants.

Finally, a last series of pots not treated with any foreign substance, was kept as control.

All the series of pots were kept under observation in an environment conditioned at temperatures comprised between 15° C. and 24° C. with a relative humidity of 70%, a photoperiod of 12 hours and a light intensity of 2.500 lux.

Every two days all the pots were uniformly watered so as to ensure a degree of humidity sufficient for a good development of the plants.

After 14 (and 21) days from the treatment, observations on the vegetative state of the plants were made using evaluations expressed on the basis of a value scale ranging from 0 (=growth equal to that of the control plants) to 4 (=complete stop of the growth).

In the Table which follows there are recorded the results obtained under each of the indicated conditions and for each plant studied.

As appears clearly from the Table:

(1) both tested herbicides proved to be phytotoxic with respect to maize, showing a degree of toxicity at about 3 at the dosage of 4 Kg/ha.;

(2) the application of either one of the two herbicides HS 26910 and "Antor" in a dose of 4 Kg/ha in combination with either the one or the other of the two substances M 7601 and M 8069, in doses of from 0.2 to 0.8 Kg/ha, eliminates completely the damage caused to the maize by the two herbicides applied singly, without however, reducing the herbicide activity against the infesting plants;

(3) the damage caused to the maize by the application of either the one or the other of the two herbicides, HS 26910 and "Antor", at a dose of 4 Kg/ha, is attenuated in a proportional way by the addition of increasing doses of antidote R-25788, without, however, being completely eliminated even at the dose of 0.8 Kg/ha.

water as was necessary for a good germination of the seeds. Immediately thereafter a series of these pots was treated with the herbicide N-(2-methyl-6-ethyl-phenyl)-N-(isopropyl-carboxymethyl)-chloroacetamide (mark: HS 26910), in the form of a hydroacetonic dispersion (20% vol/vol), in a dose of 4 kg/ha of active principle, by superficial application to the soil followed by the covering up of it with a 0.5 cm layer of further soil.

A second series of pots was treated under the same conditions, with the herbicide N-(2,6-diethyl-phenyl)-N-(ethyl-carboxymethyl) chloroacetamide (Antor, Hercules) in the same dose.

A third and a fourth set of pots were then treated, under the same conditions, with hydroacetonic dispersions respectively containing herbicide HS 26910 and herbicide Antor, each of which was added with antidotes M 8990 and, separately, to M 8991, in different ratios so as to always obtain a dose of 4 kg/ha of herbicide together with a dose of 0.05 to 0.4 kg/ha of one or of the other antidotes.

For comparison purposes, still another two sets of pots were treated under the same conditions with two hydroacetonic dispersions containing respectively herbicide HS 26910 and Antor, each of which, additioned with antidote N-diallyl-dichloroacetamide (mark: R 25788 Stauffer) in the same proportions used for the two antidotes M 8990 and M 8991.

Still another set of pots in which only maize was sown, was treated with a hydroacetonic dispersion of

TABLE I

Herbicide activity of the N-di-substituted glycines on infesting plants and on maize, in comparison with the activity in the presence of antidotes according to the invention and according to the French Patent Application No. 2,133,793.

| Substances applied | Dose Kg/ha | Infesting plants(*) at 21 days from treatment | | | | | | | | Maize 14 days from treatment | 21 days from treatment |
|---|---|---|---|---|---|---|---|---|---|---|---|
| | | E. | A. | L. | SO. | SE. | V. | R. | G. | | |
| HS 26910 | 4 | 4 | 4 | 4 | 4 | 4 | 4 | 4 | 4 | 3 | 3 |
| HS 26910 + M 7601 | 4 + 0.1 | | | | | " | | | | 1 | 1 |
| HS 26910 + M 7601 | 4 + 0.2 | | | | | " | | | | 0 | 0 |
| HS 26910 + M 7601 | 4 + 0.4 | | | | | " | | | | 0 | 0 |
| HS 26910 + M 7601 | 4 + 0.8 | | | | | " | | | | 0 | 0 |
| HS 26910 + M 8069 | 4 + 0.1 | | | | | " | | | | 2 | 2 |
| HS 26910 + M 8069 | 4 + 0.2 | | | | | " | | | | 1 | 1 |
| HS 26910 + M 8069 | 4 + 0.4 | | | | | " | | | | 1 | 1 |
| HS 26910 + M 8069 | 4 + 0.8 | | | | | " | | | | 0 | 0 |
| HS 26910 + R 25788 | 4 + 0.1 | | | | | " | | | | 2.5 | 2.5 |
| HS 26910 + R 25788 | 4 + 0.2 | | | | | " | | | | 2 | 2 |
| HS 26910 + R 25788 | 4 + 0.4 | | | | | " | | | | 1 | 1 |
| HS 26910 + R 25788 | 4 + 0.8 | | | | | " | | | | 1 | 1 |
| Antor | 4 | | | | | " | | | | 3 | 3 |
| Antor + M 7601 | 4 + 0.1 | | | | | " | | | | 1 | 1 |
| Antor + M 7601 | 4 + 0.2 | | | | | " | | | | 0 | 0 |
| Antor + M 7601 | 4 + 0.4 | | | | | " | | | | 0 | 0 |
| Antor + M 7601 | 4 + 0.8 | | | | | " | | | | 0 | 0 |
| Antor + M 8069 | 4 + 0.1 | | | | | " | | | | 2 | 2 |
| Antor + M 8069 | 4 + 0.2 | | | | | " | | | | 1 | 1 |
| Antor + M 8069 | 4 + 0.4 | | | | | " | | | | 1 | 1 |
| Antor + R 25788 | 4 + 0.1 | | | | | " | | | | 2.5 | 2.5 |
| Antor + R 25788 | 4 + 0.2 | | | | | " | | | | 1.5 | 2 |
| Antor + R 25788 | 4 + 0.4 | | | | | " | | | | 1 | 1.5 |

(*)E. = *Echinochloa crusgalli*;
A. = *Avena fatua*;
L. = *Lolium italicum*;
SO. = *Sorghum spp.*;
SE. = *Setaria glauca*;
V. = *Vigna sinensis*;
R. = *Rumex crispus*;
G. = *Galinsoga parviflora*.

EXAMPLE 11

Into a set of pots, having an upper diameter of 10 cm and a height of 10 cm, and containing sandy soil, and in each of which there had been sown a certain infesting weed (see Table II) and maize there was added as much antidotes M 8990 and M 8991 only, in doses varying from 0.05 to 0.4 kg/ha. This application had no negative effects on the maize plants.

A last set of pots was kept as witness, without any kind of treatment with foreign substances. All the sets of pots were kept under observation in a conditioned environment maintained at a temperature comprised between 15° C. and 24° C., with a relative humidity of 70%, with a light period of 12 hours and with a luminous intensity of 2500 lux.

Every two days, all pots were uniformly sprinkled so as to ensure a degree of humidity sufficient for a satisfactory growth of the plants.

After 14 and 21 days after the treatment, there were carried out determinations of the vegetative state of the plants with evaluations expressed in terms of a scale of values ranging from 0 (equal to a growth equal to that of the witness plants) up to 4 (equal to a complete stop of the growth).

In the following Table II there have been recorded the results obtained under each of the indicated conditions, and for each plant that has been studied.

From Table II the following appears quite clearly, i.e., (1) both tested herbicides proved phytotoxic for maize showing a toxicity degree of around 3 or 4 at a dose of 4 kg/ha;

(2) the application of either one of the two herbicides, HS 26910 and Antor at the dose of 4 kg/ha in addition with one or the other of the substances, M 8990 or M 8991, in doses from 0.1 to 0.4 kg/ha, eliminates completely the damage caused to the maize by the two herbicides applied singly, without, however, reducing the herbicide activity against the infesting weeds;

(3) the damage inflicted to maize by the application of either one of the two herbicides HS 26910 and Antor, in doses of 4 kg/ha is attenuated proportionally to the addition of growing doses of antidote R-25788, without, however, being completely eliminated even by the dose of 0.4 kg/ha.

(4) the two antidotes according to the invention develop a protective activity on the maize at least double than that of the compounds claimed in DOS No. 2,747,814.

TABLE II

Herbicide activity of the esters of N-N-disubstituted glycine on infesting weeds and on maize compared to the activity in the presence of antidotes according to the present invention and according to U.S. Pat. No. 4,021,224 and DOS 2,747,814

| Applied Substance | Dose kg/ha | Infesting Plants (**) after 21 days from treatment | | | | | | | | MAIZE | |
|---|---|---|---|---|---|---|---|---|---|---|---|
| | | E | A | L | SO | SE | V | R | G | After 14 days from treatment | After 21 days from treatment |
| HS 26910 | 4 | 4 | 4 | 4 | 4 | 4 | 4 | 4 | 4 | 3 | 3 |
| HS 26910 + M 8990 | 4 + 0.4 | | | | " | | | | | 0 | 0 |
| " | 4 + 0.2 | | | | " | | | | | 0 | 0 |
| " | 4 + 0.1 | | | | " | | | | | 0 | 0 |
| " | 4 + 0.05 | | | | " | | | | | 0.5 | 0.5 |
| HS 26910 + M 8991 | 4 + 0.4 | | | | " | | | | | 0 | 0 |
| " | 4 + 0.2 | | | | " | | | | | 0 | 0 |
| " | 4 + 0.1 | | | | " | | | | | 0 | 0 |
| " | 4 + 0.05 | | | | " | | | | | 0.5 | 0.5 |
| HS 26910 + M 7601(***) | 4 + 0.4 | | | | " | | | | | 0 | 0 |
| " | 4 + 0.2 | | | | " | | | | | 0 | 0 |
| " | 4 + 0.1 | | | | " | | | | | 1 | 1 |
| " | 4 + 0.05 | | | | " | | | | | 1.5 | 1.5 |
| HS 26910 + R 25768(*) | 4 + 0.4 | | | | " | | | | | 1 | 1 |
| " | 4 + 0.2 | | | | " | | | | | 2 | 2 |
| HS 26910 + R 25788(*) | 4 + 0.1 | | | | " | | | | | 2.5 | 2.5 |
| " | 4 + 0.05 | | | | " | | | | | 2.5 | 2.5 |
| ANTOR | 4 | | | | " | | | | | 3 | 3 |
| ANTOR + M 8990 | 4 + 0.4 | | | | " | | | | | 0 | 0 |
| " | 4 + 0.2 | | | | " | | | | | 0 | 0 |
| " | 4 + 0.1 | | | | " | | | | | 0 | 0 |
| " | 4 + 0.05 | | | | " | | | | | 0 | 0 |
| ANTOR + M 8991 | 4 + 0.4 | | | | " | | | | | 0 | 0 |
| " | 4 + 0.2 | | | | " | | | | | 0 | 0 |
| " | 4 + 0.1 | | | | " | | | | | 0 | 0 |
| " | 4 + 0.05 | | | | " | | | | | 0 | 0 |
| ANTOR + M 7601(***) | 4 + 0.4 | | | | " | | | | | 0 | 0 |
| " | 4 + 0.2 | | | | " | | | | | 0 | 0 |
| " | 4 + 0.1 | | | | " | | | | | 1 | 1 |
| " | 4 + 0.05 | | | | " | | | | | 1.5 | 2 |
| ANTOR + R 25788(*) | 4 + 0.4 | | | | " | | | | | 1 | 1.5 |
| " | 4 + 0.2 | | | | " | | | | | 1.5 | 2 |
| " | 4 + 0.1 | | | | " | | | | | 2.5 | 2.5 |
| " | 4 + 0.05 | | | | " | | | | | 2.5 | 2.5 |

(*)COMPARATIVE ANTIDOTE (U.S. Pat. No. 4,021,224)
(**)E = echinocloa cruss-galli; A = Avena fatua; L = Loliul italicum; SO = Sorghum spp; SE = Setaria glauca; V = Vigna sinensis; R = Rumex crispus; G = Galensoga parvifera.
(***) = Comparative antidote (DOS 2,747,814)

What is claimed is:

1. Method for combatting infesting plants of a maize cultivation without damaging the maize, which comprises treating the infested maize with from 3 to 5 kg/ha of herbicidal N-di-loweralkyl phenyl, N-chloroacetylglycines and with, depending on the quantity of said herbicidal N-substituted glycines used, from at least 0.05 to 0.125 kg/ha. of an antidote having the general formula

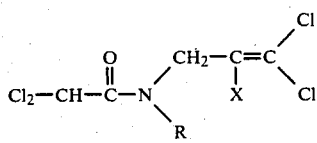

in which
X is chlorine; and
R is a methyl, ethyl, allyl, 3,3-dichloroallyl, 2,3,3-trichloroallyl, or 1,1-dimethylpropargyl group.

2. The method of claim 1, in which the antidote is N-allyl-N-(3,3-dichloroallyl)-dichloroacetamide.

3. The method of claim 1, in which the antidote is N-methyl-N-(2,3,3-trichloroallyl)-dichloroacetamide.

4. The method of claim 1, in which the antidote is N-(3,3-dichloroallyl)-N-ethyl-dichloroacetamide.

5. The method of claim 1, in which the antidote is N-(1,1-dimethyl propargyl)-N-(3,3-dichloroallyl)-dichloroacetamide.

6. Herbicidal compositions which are non-toxic to maize, comprising an effective amount of N-diloweralkylphenyl, N-chloroacetylglycines and, as antidotes for said herbicidal N-substituted glycines, compounds of the formula

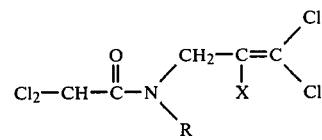

in which
X is chlorine; and
R is a methyl, ethyl, allyl, 3,3-dichloroallyl, 2,3,3-trichloroallyl or 1,1-dimethylpropargyl group,
said antidotes being present in the compositions in an amount of from 5% to 20% by weight with respect to said herbicidal N-substituted glycines.

7. Herbicidal compositions according to claim 6, in which the antidote is N-allyl-N-(3,3-dichloroallyl)-dichloroacetamide.

8. Herbicidal compositions according to claim 6, in which the antidote is N-methyl-1-N-(2,3,3-trichloroallyl)-dichloroacetamide.

9. Herbicidal compositions according to claim 6, in which the antidote is N-(3,3-dichloroallyl)-N-ethyl-dichloroacetamide.

10. Herbicidal compositions according to claim 6, in which the antidote is N-(1,1-dimethylpropargyl) N-(3,3-dichloroallyl)-dichloroacetamide.

* * * * *